United States Patent
Ahmad et al.

(10) Patent No.: US 9,167,971 B2
(45) Date of Patent: Oct. 27, 2015

(54) HEART MURMUR EXTRACTION AND HEART IMPAIRMENTS IDENTIFICATION USING FUZZY CONTROLLER

(71) Applicant: COMSATS Institute of Information Technology, Abbottabad (PK)

(72) Inventors: Muhammad Sheraz Ahmad, Abbottabad (PK); Khurram Aziz, Abbottabad (PK); Shahid Khattak, Abbottabad (PK)

(73) Assignee: COMSATS Institute of Information Technology, Abbottabad (PK)

( * ) Notice: Subject to any disclaimer, the term of this patent is extended or adjusted under 35 U.S.C. 154(b) by 62 days.

(21) Appl. No.: 14/098,067

(22) Filed: Dec. 5, 2013

(65) Prior Publication Data

US 2015/0157218 A1      Jun. 11, 2015

(51) Int. Cl.
*A61B 5/02* (2006.01)
*A61B 5/00* (2006.01)
*A61B 7/04* (2006.01)

(52) U.S. Cl.
CPC ........... *A61B 5/02028* (2013.01); *A61B 5/7203* (2013.01); *A61B 5/7264* (2013.01); *A61B 7/04* (2013.01)

(58) Field of Classification Search
CPC .......... A61B 7/04; A61B 7/00; A61B 5/0205
USPC .................................. 600/528, 9, 8
See application file for complete search history.

(56) References Cited

U.S. PATENT DOCUMENTS

| | | | |
|---|---|---|---|
| 2005/0222515 A1* | 10/2005 | Polyshchuk et al. | 600/528 |
| 2006/0142667 A1* | 6/2006 | Munk | 600/528 |
| 2010/0145210 A1* | 6/2010 | Graff et al. | 600/528 |

* cited by examiner

*Primary Examiner* — Christopher D Koharski
*Assistant Examiner* — Philip Edwards
(74) *Attorney, Agent, or Firm* — H.C. Park & Associates, PLC

(57) ABSTRACT

A method and device for heart murmur extraction and classification is disclosed. Data corresponding to a heart sound/signal is acquired from a patient through a data acquirer. The heart sound data is processed to isolate systole and diastole periods. Features to discriminate between the defects types associated with different heart murmurs are extracted, and the heart murmurs are detected and identified based on the extracted features using a fuzzy controller.

8 Claims, 5 Drawing Sheets

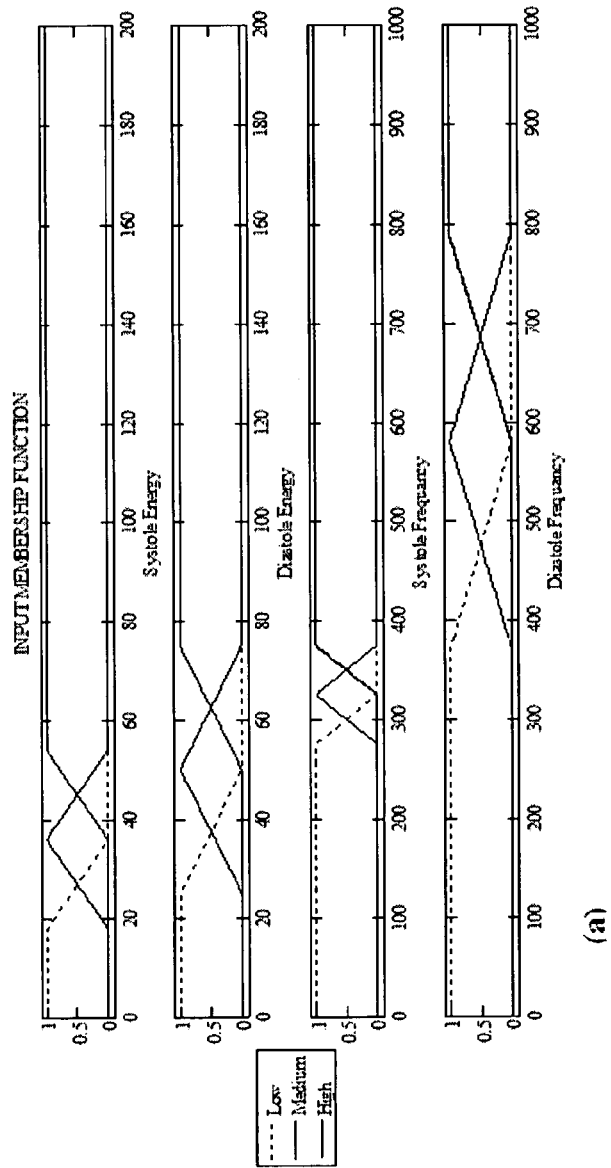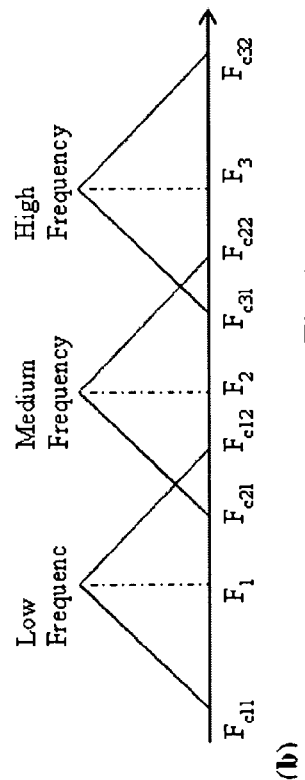
Fig. 4

| Rule No | $S_f$ | $D_f$ | $S_a$ | $D_a$ | Output1 Normal | Output2 AR | Output3 MS | ... | Output4 AS |
|---|---|---|---|---|---|---|---|---|---|
| 1 | L | L | L | L | H | L | L | ... | L |
| 2 | L | L | L | M | L | M | H | ... | L |
| 3 | L | L | L | H | L | H | M | ... | L |
| 4 | L | L | M | L | L | L | L | ... | H |
| 5 | L | L | M | M | L | L | M | ... | M |
| 6 | L | L | M | H | L | H | M | ... | L |
| 7 | L | L | H | L | L | L | L | ... | H |
| 8 | L | L | H | M | L | L | M | ... | H |
| 9 | L | L | H | H | L | L | M | ... | H |
| 10 | L | M | L | L | H | L | L | ... | L |
| 11 | L | M | L | M | L | H | L | ... | L |
| 12 | L | M | L | H | L | H | L | ... | L |
| 13 | L | M | M | L | L | M | H | ... | M |
| 14 | L | M | M | M | L. | L | H | ... | M |
| 15 | L | M | M | H | L | H | M | ... | L |
| ⋮ | ⋮ | ⋮ | ⋮ | ⋮ | ⋮ | ⋮ | ⋮ | ⋮ | ⋮ |
| 70 | H | M | H | L | L | L | L | ... | H |
| 71 | H | M | H | M | L | L | M | ... | H |
| 72 | H | M | H | H | H | H | M | ... | L |
| 73 | H | H | L | L | L | L | L | ... | L |
| 74 | H | H | L | M | L | M | H | ... | L |
| 75 | H | H | L | H | L | H | M | ... | L |
| 76 | H | H | M | L | L | L | L | ... | H |
| 77 | H | H | M | M | L | L | H | ... | M |
| 78 | H | H | M | H | L | H | M | ... | L |
| 79 | H | H | H | L | L | L | L | ... | H |
| 80 | H | H | H | M | L | L | M | ... | H |
| 81 | H | H | H | H | L | H | M | ... | L |

Fig. 5  Rule Table (L=low, M=Medium, H=High)

HEART MURMUR EXTRACTION AND HEART IMPAIRMENTS IDENTIFICATION USING FUZZY CONTROLLER

BACKGROUND

1. Field

Exemplary embodiments of the present disclosure relate to a method and system of heart murmur extraction and identification of heart impairments through signal processing techniques.

2. Discussion

Functions of a human body may be transduced and/or detected in many ways to provide signals that may be interpreted to form an assessment of the human condition. Conventional transduction methods can be used to collect data via different instruments, such as stethoscopes, Ultrasound machines, and Magnetic Resonance Imaging (MRI) machines.

However, one limitation on relying on conventional specialized instruments to perform transduction methods is the lack of specialized medical professionals (who know how to operate the specialized instruments and/or understand data produced by the specialized instruments) in rural and urban clinics/hospitals in, for example, various developing countries. Accordingly, there is a need for providing a simplified transduction method and system that may be used by lay men. Furthermore, specialized instruments, such as MRI and Ultrasound machines, may be very expensive and unaffordable for many medical professionals.

In addition, information obtained by medical instruments may not always be clear. For example, information related to a heartbeat or signal may be acquired using a stethoscope. However, the signal may be weak and/or masked by surrounding noises thereby leading to a false diagnosis. The signal processing techniques can be employed in order to enhance the quality of the information acquired which can then be used to predict different pathological conditions.

The above information disclosed in this Background section is provided to enhance understanding of the background of the disclosed subject matter and therefore may contain information that does not form any part of the prior art nor what the prior art may suggest to a person of ordinary skill in the art

SUMMARY

Exemplary embodiments of the present disclosure overcome the lack of specialized medical professionals in rural and urban medical facilities by disclosing a method and system for acquiring a heart sound/signal from a person, and identifying the nature of a heart murmur.

Additional features of the present disclosure will be set forth in the description which follows, and, in part, will be apparent from the description, or may be learned by practice of the disclosed subject matter.

Exemplary embodiments of the present disclosure disclose a method including receiving audio data associated with a heart signal, extracting, using a processor, features within the data corresponding to at least one of a systolic cycle and a diastolic cycle, and determining a nature of a heart murmur based on the extracted features.

It is to be understood that both the foregoing general description and the following detailed description are exemplary and explanatory and are intended to provide further explanation of the disclosed subject matter as claimed.

BRIEF DESCRIPTION OF THE DRAWINGS

The accompanying drawings, which are included to provide a further understanding of the disclosed subject matter and are incorporated in and constitute a part of this specification, illustrate exemplary embodiments of the disclosed subject matter, and together with the description serve to explain the principles of the disclosed subject matter.

FIG. 4 shows (a) membership functions used for fuzzification of distinguishing features such as energies and dominant frequencies in the systole and diastole regions, and (b) a generic membership function showing the notation used for cut-off and central frequencies, according to exemplary embodiments of the present disclosure.

FIG. 5 is a sample rule-based protocol having four inputs each with three linguistic regions and four outputs, according to exemplary embodiments of the present disclosure.

DETAILED DESCRIPTION OF THE ILLUSTRATED EMBODIMENTS

Figure 1:
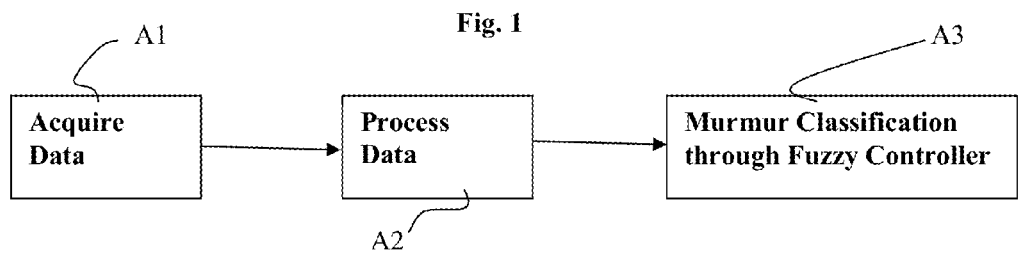
FIG. 1 is a block diagram illustrating a method for heart murmur extraction and classification according to exemplary embodiments of the present disclosure.

The disclosed subject matter is described more fully hereinafter with reference to the accompanying drawings, in which exemplary embodiments of the disclosed subject matter are shown. This disclosed subject matter may, however, be embodied in many different forms and should not be construed as limited to the exemplary embodiments set forth herein. Rather, these exemplary embodiments are provided so that this disclosure is thorough, and will fully convey the scope of the disclosed subject matter to those skilled in the art. In the drawings, the size and relative sizes of layers and regions may be exaggerated for clarity Like reference numerals in the drawings denote like elements.

It will be understood that when an element or layer is referred to as being "on" or "connected to" another element or layer, it can be directly on or directly connected to the other element or layer, or intervening elements or layers may be present. In contrast, when an element is referred to as being "directly on" or "directly connected to" another element or layer, there are no intervening elements or layers present. It may also be understood that for the purposes of this disclosure, "at least one of X, Y, and Z" can be construed as X only, Y only, Z only, or any combination of two or more items X, Y, and Z (e.g., XYZ, XYY, YZ, ZZ).

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the present disclosure.

The terminology used herein is for the purpose of describing exemplary embodiments only and is not intended to be limiting of the disclosed subject matter. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments of the disclosed subject matter are described in detail with reference to the accompanying drawings.

Figure 3:
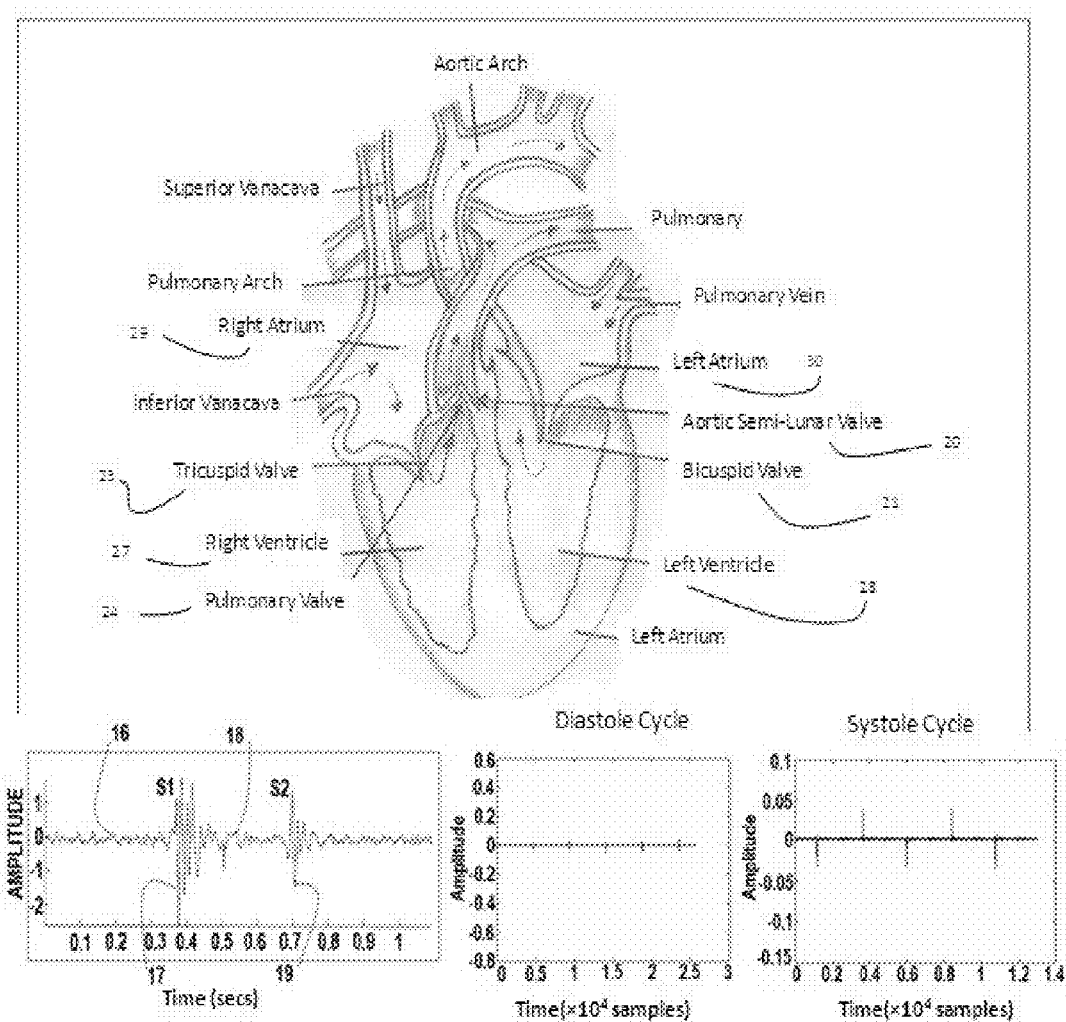
FIG. 3 is a sectional view of the heart showing different valves and a complete heart murmur signal and its segmented systole and diastole regions, according to exemplary embodiments of the present disclosure.

As shown in FIG. 3, a human heart is made up of four chambers, namely a right ventricle 27, a left ventricle 28, a right atrium 29, and a left atrium 30. A complete cardiac cycle may include a diastole period 16, a first heart sound S1 17, a systole period 18, and a second heart sound S2 19.

A heart murmur may be an extra or unusual sound detected in a cardiac cycle. Murmurs may range from faint to loud, and may sound like a whooshing or swishing sound. There are two dominant audible heart signals/sounds, the first heart sound S1 17 and the second heart sound S2 19. The first heart sound S1 17 may be associated with a closing of the bicuspid 21 and tricuspid valves 23. The second heart sound S2 19 may be associated with a closing of the aortic 20 and pulmonary valves 24.

The interval 18 between the first heart sound S1 17 and the second heart sound S2 19 corresponds to a ventricular systole and the interval 16 between the second heart sound S2 19 and a subsequent first heart sound S1 17 corresponds to a ventricular diastole. When no unusual heart activity occurs, both intervals 16 and 18 may be silent. Murmurs, which are caused by certain cardiovascular defects and diseases, may occur in these intervals 16, 18.

The murmurs that lie in interval 18 between the first heart sound S1 17 and the second heart sound S2 19 are known as systolic murmurs. Systolic murmurs may be divided into two categories, systolic ejection murmurs and pan-systolic murmurs. The murmurs that lie in the interval 16 between the second heart sound S2 and a subsequent first heart sound S1 are known as diastolic murmurs.

Referring to FIG. 1, a method for heart murmur extraction and classification is described.

Data (e.g., at least one signal corresponding to a heart movement or sound) is acquired from a person through a data acquirer (A1). The acquired data may be processed (A2), using a processor, to isolate the diastole period 16 and the systole period 18 to extract features required to determine if a defect associated with different heart murmurs is present. After the data is processed, the extracted features may be classified using a fuzzy controller to detect a presence of a pathological heart murmur (A3).

Figure 2:
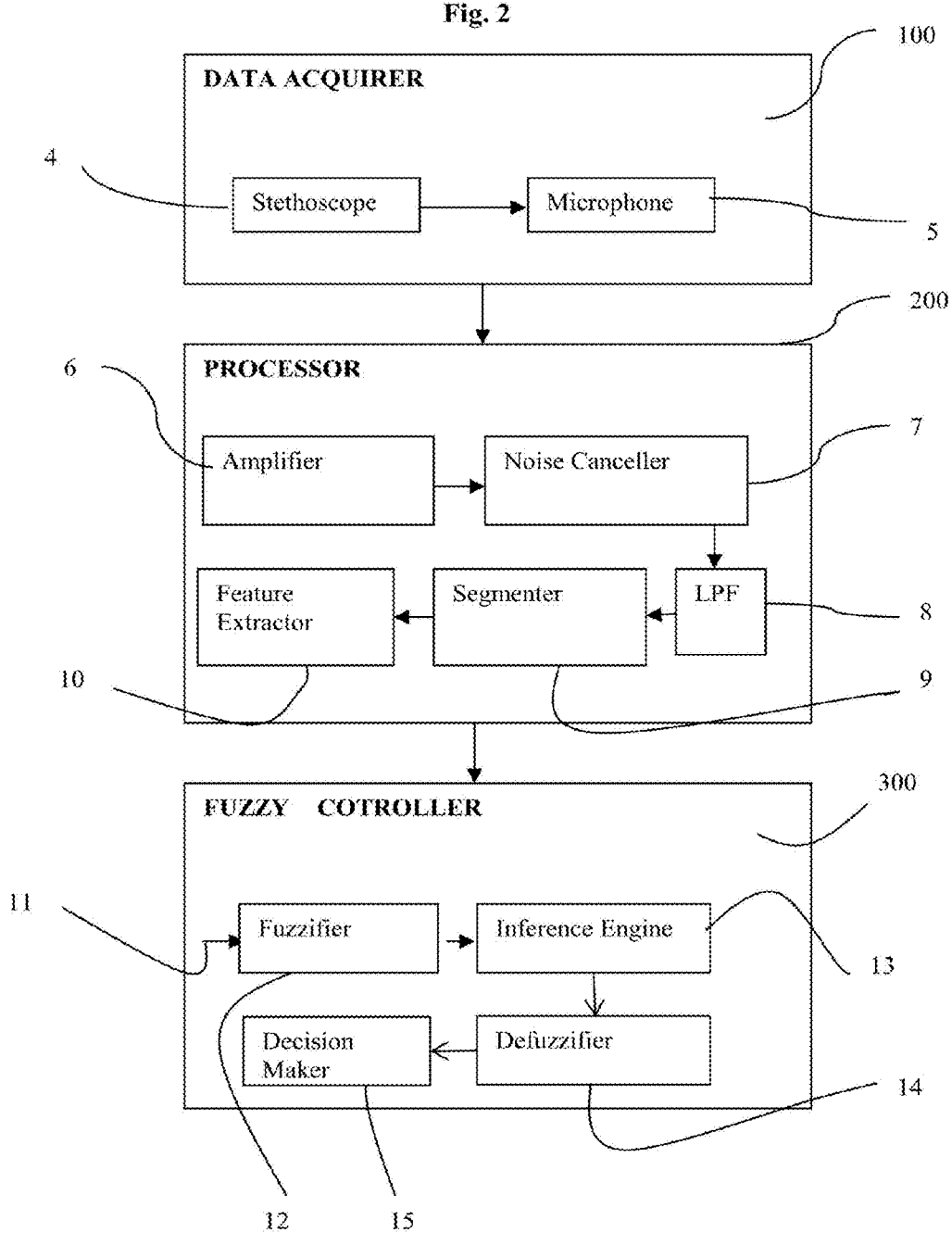
FIG. 2 illustrates a system for heart murmur extraction and classification according to exemplary embodiments of the present disclosure.

Referring to FIG. 2, a system for heart murmur extraction and classification is described. The device may include a data acquirer 100, a processor 200, and a Fuzzy controller 300.

The data acquirer 100 may acquire data related to heart activities and sounds from a person (e.g., patient). Various suitable devices or combination of devices including, for example, a stethoscope used together with a microphone (or any appropriate sound transducer) may be used as the data acquirer 100. In general, a front-end of the data acquirer 100 may include a chest piece with a mechanical setup to receive sound waves from a person's chest while shielding the received sound waves from ambient noises. The sound may be transduced at the backend of the data acquirer 100 into electrical signals by using various suitable devices, including, for example, a microphone 5.

As an example, an acoustic stethoscope 4 may receive sound waves from a person's chest via a chest piece. The chest piece may consist of two sides, a diaphragm (plastic disc) and a bell (hollow cup). The chest piece may be placed on a person in an area corresponding to the person's heart for sensing the person's heart sound signal. When the diaphragm is placed on the person, a sound from the person's body (e.g., heart) may cause the diaphragm to vibrate creating acoustic pressure waves that travel through the hollow tubes of a stethoscope 4 to the microphone 5. The sound from the person's body may correspond to a sound generated by movement of the person's heart, as described above.

Referring to FIG. 2, a processor 200 may include an Amplifier 6, a Noise Canceller 7, a Low-pass Filter (LPF) 8, a Segmenter 9, and a Feature Extractor 10.

The amplifier 6 may amplify signals corresponding to heart sounds and/or movements acquired through the data acquirer 100. Amplification of the received signals may be performed using various suitable amplifiers, including, for example, a Bio-Amplifier that is a differential instrumentation amplifier.

In general, signals obtained from a microphone (e.g., microphone 5) may contain noise. The noise may originate at the stethoscope 4's diaphragm or may be inherent in the environment surrounding the person. Accordingly, a noise canceller 7 may be used to remove or reduce the noise in the received signals. In some cases, an adaptive filter may be used as the noise canceller 7. The adaptive filter is used to isolate the useful/relevant information from the noise in a signal (i.e., acquired data) using any suitable adaptive filtering technique. Adaptive filtering may control the characteristics of a filter output signal by conditioning a signal input to the filter. For instance, filter coefficients may be updated by an adaptive algorithm to optimize the filter response to a desired performance criterion. The adaptive filter may adjust and compensate for changes in the input signal, output signal, or system parameters.

As an example, the adaptive filter may receive two inputs. A first input of the adaptive filter may correspond to a heart signal and ambient noise, and a second input may correspond to just the ambient noise. The adaptive filter may correlate these two signals in order to reconstruct the undesired signal, which is then subtracted out of the noisy heart signal.

An output of the noise canceller 7 may be provided to the low-pass filter (LPF) 8. A cutoff frequency of the low-pass filter 8 may be adjusted to accommodate the innocent and pathological heart murmurs while mitigating high frequency sounds (1 KHz and above). Since a frequency of signals corresponding to heart murmurs resides in a low frequency range from 20-1,000 Hz, undesirable high frequency noise can be suppressed using the low-pass filter 8. As an example, a filter with a stop-band frequency of up to 1.5 KHz may be used.

After the received signal is low-pass filtered, the received signal may be segmented by a segmenter 9 into a diastole cycle 25 and a systole cycle 26 using spectral analysis of the signal corresponding to the heart sound. The segmenter 9 may temporally separate the signal corresponding to the heart sound into component cycles of the systole period 26 and diastole period 25 by isolating low frequency data. The segmenter 9 may accurately identify the position of the first heart sound S1 17 and the second heart sound S2 19, and based on the identified first heart sound S1 17 and second heart sound S2 19, the systole period 18 and diastole period 16 may be determined.

For example, an algorithm using wavelet transform and normalized Shannon energy may be used to identify positions of different segments within audio data. Shannon energy may enhance the lower frequencies, which may include the first heart sound S1 17 and the second heart sound S2 19. Distinct peaks for the first heart sound S1 17 and the second heart sound S2 19 may be obtained. These steps may be repeated in a quasi-periodic fashion. The peaks and regions around where a signal level exceeds a threshold may be determined to be the first heart sound S1 17 and the second heart sound S2 19.

After the first heart sounds S1 17 and the second heart sounds S2 19 have been determined, in some cases, the processor 200 may determine that a larger of two intervals in a received, segmented signal is the diastole interval 16, and a smaller of the two intervals in the received, segmented signal is the systole interval 18, which may be relatively constant compared to the diastole interval 16. The processor 200 determines that an interval between the first heart sound S1 17 and the second heart sound S2 19 corresponds to the systole interval 18, and that an interval before a first heart sound S1 17 and after a second heart sound S2 19 corresponds to the diastole interval 16. Starting from a largest interval of a received, segmented signal, the processor 200 may examine various intervals in the received, segmented signal, both before and after the largest interval, to determine the relative consistency of the systole and diastole intervals 16, 18 using different tolerances.

Diastole and systole cycles 25 and 26 may be separated from the received signal to extract the accumulative energy and frequency information of systole intervals 18 and diastole intervals 16.

Referring to FIG. 2, the feature extractor 10 may receive the received, segmented signal from the segmenter 9. Since heart artifacts may be identified using energy and dominant frequency features present within each component cycle, the Max Energy and the centeriod frequency within diastole cycles 25 and systole cycle 26 have been extracted according to exemplary embodiments of the present disclosure.

The feature extractor 10 may employ a Fourier transform to the signals received from segmenter 9 to translate the two temporal signals corresponding to the diastole cycle 25 and the systole cycle 26 into the frequency domain. As an example, the Fourier transform for a continuous time signal x(t) may be expressed according to Equation (1).

$$X(\omega) = \int_{-\infty}^{\infty} x(t) e^{-j\omega t} dt \quad (1)$$

Power spectral density provides information about the signal power in the frequency domain. The power spectral density may be calculated using the magnitude complex Fourier transformed signal, and may be expressed according to Equation (2).

$$S_f(\omega) = \frac{1}{\pi} \left| X\left(\frac{\omega}{2\pi}\right) \right|^2 \quad (2)$$

The features required to discriminate between different pathological murmurs may be obtained by passing the systole cycle 26 and the diastole cycle 25 through three filter banks shown in FIG. 4(b).

The centroid frequency value of systole energy may be determined using Equation (3). The centroid frequency value of diastole energy may be determined using Equation (4).

$$S(f) = \frac{F_1 \times S_{e1} + F_2 \times S_{e2} + F_3 \times S_{e3}}{F_1 + F_2 + F_3} \quad (3)$$

$$D(f) = \frac{F_1 \times D_{e1} + F_2 \times D_{e2} + F_3 \times D_{e3}}{F_1 + F_2 + F_3} \quad (4)$$

S(f) is the centroid frequency of systole cycles 26. D(f) is the centroid frequency of diastole cycles 25. $Se_k$, $De_k$ are the energy of a systole cycle 26 and a diastole cycle 25, respectively, in band k (where k may be any whole number greater than 1). The frequency $F_k$ may be determined using Equation (5).

$$F_k = \frac{F_{ck1} + F_{ck2}}{2}. \quad (5)$$

$F_{ck1}$ and $F_{ck2}$ are the lower and upper cut off frequencies for the $k^{th}$ filter.

The processor 200 may calculate a systole energy value Se and a diastole energy value De using Equations (6) and (7), respectively.

$$S_e = \max[S_{e1}, S_{e2}, S_{e3}] \quad (6)$$

$$D_e = \max[D_{e1}, D_{e2}, D_{e3}] \quad (7)$$

The systole energy value Se and diastole energy value De may be provided to the fuzzy controller 300. The fuzzy controller 300 may be configured to detect the presence of heart murmurs, which may be classified based on energies and frequencies.

The fuzzy controller 300 uses fuzzy logic methodology to classify different types of systole and diastole heart murmurs, such as aortic regurgitation, mitral stenosis, etc. The fuzzy controller 300 may receive the systole energy value Se, the systole centroid frequency $S_f$, the diastole energy value De, and the diastole centroid frequency $D_f$ from the processor 200, and may output a decision of whether a received heart signal has a heart murmur or corresponds to a normal heart sound.

A fuzzifier 11 of the fuzzy controller 300 converts the systole energy value Se, the systole centroid frequency $S_f$, the diastole energy value De, and the diastole centroid frequency $D_f$ into fuzzy world values in different linguistic regions (e.g., low, medium, high) as shown in FIG. 4(a).

The fuzzy world values may be provided to an inference engine 13, which may use an appropriate inference method (e.g., Mamdani/Sugeno) and apply a rule-based protocol to the fuzzy world values. The rule-based protocol may include a collection of IF-THEN rules.

The size of the rule-based protocol may depend on a number of inputs and linguistic regions used for the controller 300. In FIG. 5 a sample rule-based protocol is shown using four inputs $S_e$, $D_e$, $S_f$, $D_f$, and three linguistic regions. Four outputs corresponding to a normal heart decision, an Aortic Regurgitation (AR) decision, a Mitral Stenosis (MS) decision, and an Aortic Stenosis (AS) may be provided. It should be understood that although only four outputs have been shown in FIG. 5, in general, the rule-based protocol may be used to make various and numerous types of decisions not limited to the above-noted four outputs.

In FIG. 5, the size of rule-based protocol is 81. The size of the rule-based protocol may be calculated using Equation (8). $L_i$ represents the total number of linguistic regions of each input i, and N is the total number of entries of the rule base. The three linguistic regions for input are shown in FIG. 4(a).

$$N = L_1 \times L_2 \times L_3 \qquad (8)$$

After applying the rule-based protocol, the inference engine 13 may provide the results to a Defuzzifier 14, which may perform a defuzzification method to retranslate the fuzzy world values into crisp values. In general, various suitable defuzzification methods may be used. According to exemplary embodiments of the present disclosure, a center of gravity defuzzification method is employed as shown in equation (9).

$$\hat{x} = \frac{(\Sigma \mu(x) x)}{\Sigma \mu(x)} \qquad (9)$$

In equation (9), $\hat{x}$ is the value of running variable on x-axis, and $\mu(x)$ is the corresponding value of probability.

Number of outputs of the fuzzy controller 300 corresponds to the number of diseases to be classified.

Comparators (not shown) may be applied to the fuzzy controller 300 outputs, and a heart disease for which the output value is largest may be determined. For example, crisp values determined for each heart artifact by Defuzzifier 14 may be compared to one another by the comparators within decision maker 15, and the crisp value having a highest relative magnitude may be selected. Accordingly, a heart artifact having the highest probability may be chosen.

As can be appreciated from the exemplary embodiments, a novel method and system for providing heart murmur detection has been provided. The disclosed method and system does not require any specialized medical professional, and may be deployed to numerous rural and urban centers in a cost-efficient manner.

It will be apparent to those skilled in the art that various modifications and variations can be made to the present disclosure without departing from the spirit or scope of the disclosed subject matter. Thus, it is intended that the present disclosure cover the modifications and variations of the disclosed subject matter provided they come within the scope of the appended claims and their equivalents.

What is claimed is:

1. A method, comprising:
    receiving data associated with a heart signal;
    extracting, using a processor, features within the data corresponding to at least one of a systole cycle and a diastole cycle comprising dividing a quasi periodic heart signal into multiple regions, the multiple regions comprising the systole cycle and a diastole cycle; and
    determining a nature of a heart murmur based on the extracted features comprising:
        determining a value associated with discriminating features in the multiple regions,
        determining whether an innocent heart murmur or a pathological heart murmur is present using the discriminating features comprising a systole energy value, a diastole energy value, a systole center frequency, and a diastole center frequency, and
        converting the discriminating features comprising the systole energy value, the diastole energy value, the systole center frequency, and the diastole center frequency into fuzzy values,
    wherein the diastole center frequency of a diastole period is determined by weighing the energy in each region, and
    the discriminating features comprises a maximum energy, the maximum energy being at a different regions for systole periods and for diastole periods, the systole center frequency having a maximum energy and the diastole center frequency having a maximum energy are input to a fuzzy controller.

2. The method of claim 1, wherein receiving the data comprises:
    receiving the data via multiple sources to decouple ambient noise from the heart signal.

3. The method of claim 1, wherein the systole center frequency of a systole period is determined by weighing the energy in each region.

4. The method of claim 1, wherein the determining further comprises:
    generating a rule-based protocol.

5. The method of claim 4, wherein the determining further comprises:
    providing an output for each heart artifact, each artifact having a different rule-based protocol.

6. The method of claim 5, wherein the determining further comprises:
    converting the output for each heart artifact to a crisp value, respectively.

7. The method of claim 6, wherein the crisp value of each heart artifact corresponds to a probability of occurrence of a heart artifact.

8. The method of claim 7, wherein the determining further comprises:
    comparing the crisp values of each heart artifact; and
    selecting a crisp value having the greatest value.

* * * * *